(12) United States Patent
Meller et al.

(10) Patent No.: US 8,696,990 B2
(45) Date of Patent: Apr. 15, 2014

(54) DEVICE FOR THE PHOTOMETRIC EXAMINATION OF SAMPLES

(75) Inventors: Paul Meller, Wehrheim (DE); Holger Pufahl, Liederbach (DE)

(73) Assignee: Siemens Healthcare Diagnostics Products GmbH, Marburg (DE)

( * ) Notice: Subject to any disclaimer, the term of this patent is extended or adjusted under 35 U.S.C. 154(b) by 602 days.

(21) Appl. No.: 12/876,405

(22) Filed: Sep. 7, 2010

(65) Prior Publication Data

US 2011/0076199 A1  Mar. 31, 2011

(30) Foreign Application Priority Data

Sep. 30, 2009 (DE) .......................... 10 2009 043 524

(51) Int. Cl.
*G01N 15/06* (2006.01)

(52) U.S. Cl.
USPC ................. 422/63; 422/50; 422/52; 422/400; 422/64; 422/65; 422/66; 422/67; 422/68.1; 422/560; 422/561; 436/43; 436/174; 436/164; 436/172

(58) Field of Classification Search
USPC ............... 422/50, 52, 400, 63, 64, 65, 66, 67, 422/68.1, 560, 561; 436/43, 174, 164, 172
See application file for complete search history.

(56) References Cited

U.S. PATENT DOCUMENTS

| | | | |
|---|---|---|---|
| 4,699,766 A | 10/1987 | Yamashita | 422/64 |
| 4,848,914 A | 7/1989 | Shiraishi | 356/440 |
| 5,178,833 A | 1/1993 | Covain | 422/64 |
| 7,842,504 B2 * | 11/2010 | Devlin, Sr. | 436/47 |
| 8,038,941 B2 * | 10/2011 | Devlin, Sr. | 422/64 |
| 2005/0013736 A1 * | 1/2005 | McKeever | 422/63 |

FOREIGN PATENT DOCUMENTS

| | | | |
|---|---|---|---|
| DE | 3904201 | 5/1990 | G01N 33/50 |
| DE | 4013588 | 11/1991 | G01N 33/53 |
| EP | 0411620 A2 | 2/1991 | |
| JP | 54113382 A | 9/1979 | |
| JP | 61274268 A | 12/1986 | |
| JP | 62121365 | 6/1987 | G01N 35/02 |
| JP | 0365654 A | 3/1991 | |
| JP | 0438466 A | 2/1992 | |
| JP | 2007225339 A | 9/2007 | |

OTHER PUBLICATIONS

Japanese Office Action, Application No. 2010218809, 14 pages, Nov. 26, 2013.

* cited by examiner

*Primary Examiner* — Brian J Sines
(74) *Attorney, Agent, or Firm* — King & Spalding L.L.P.

(57) ABSTRACT

A device for the photometric examination of samples has a sample-holder apparatus for at least two sample vessels, and a measuring apparatus and a moveable apparatus. The sample-holder apparatus is designed to be stationary, and the measuring apparatus is arranged on the moveable apparatus such that it can be displaced by means of the moveable apparatus.

16 Claims, 4 Drawing Sheets

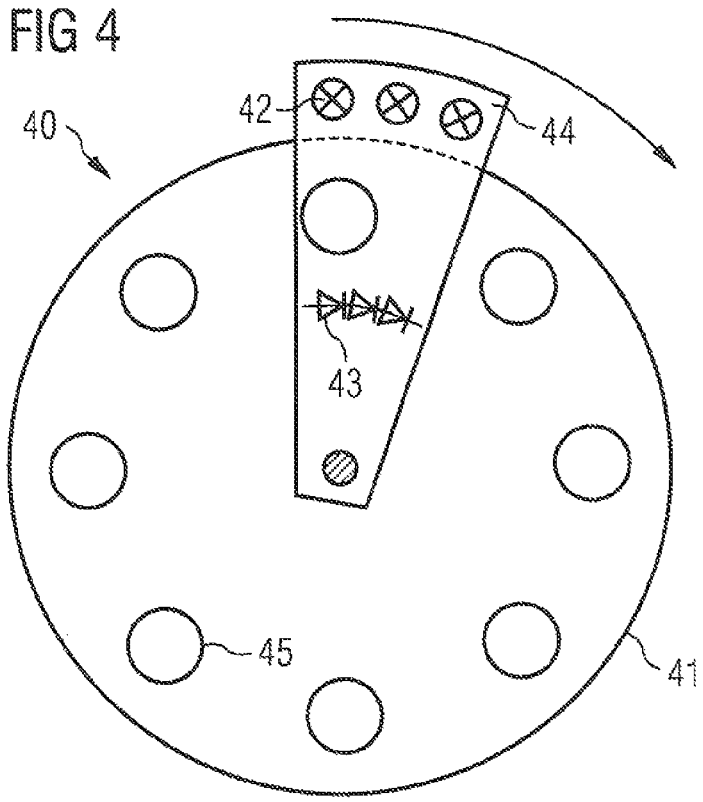
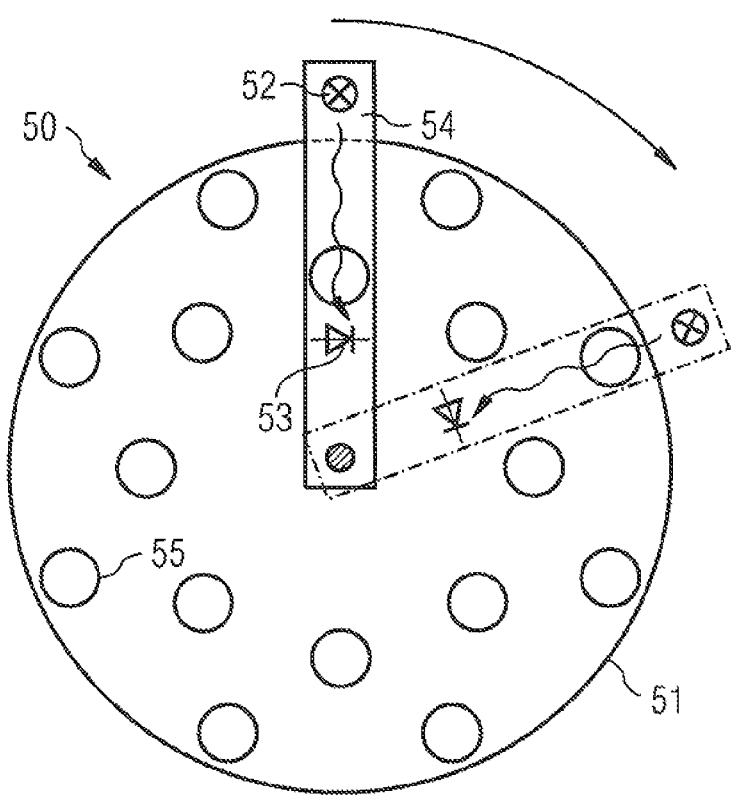

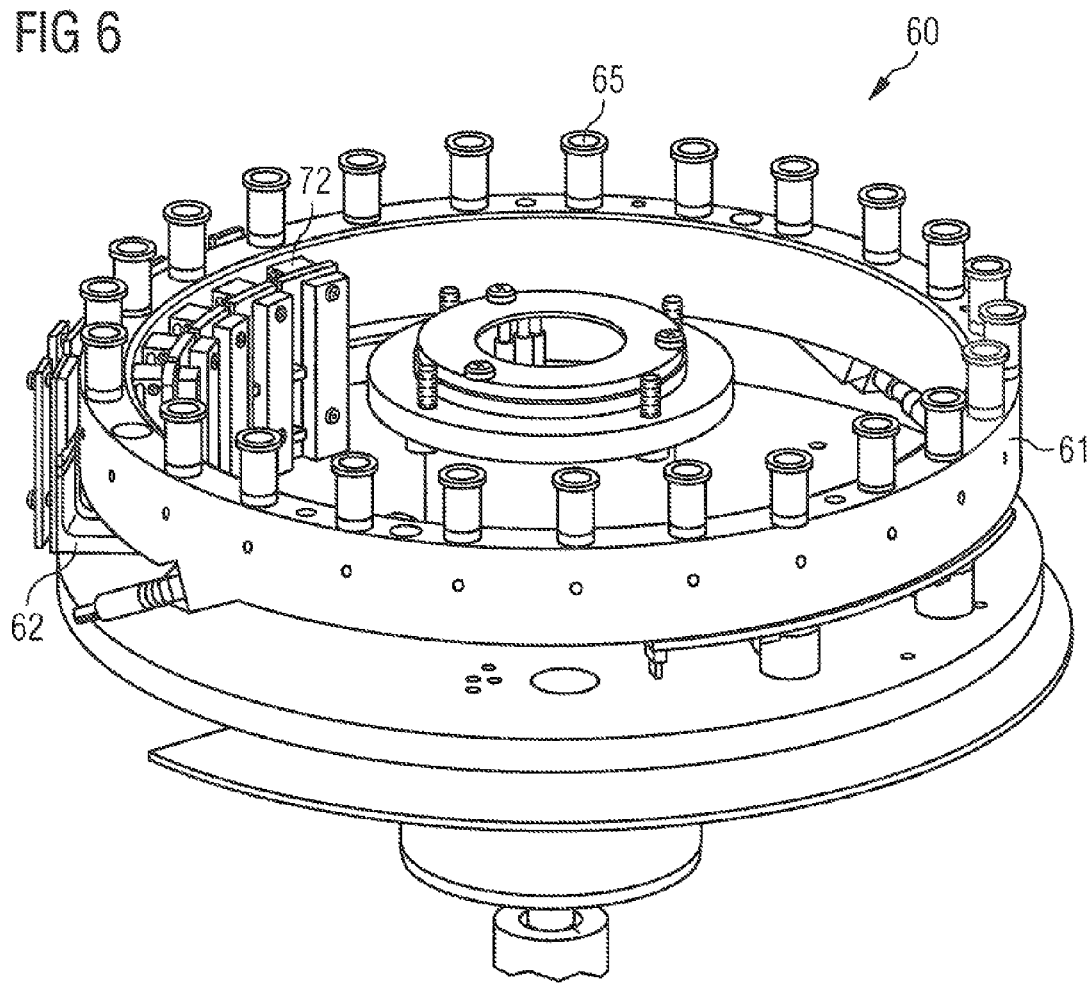

DEVICE FOR THE PHOTOMETRIC EXAMINATION OF SAMPLES

CROSS-REFERENCE TO RELATED APPLICATIONS

This application claims priority to German Patent Application No. 10 2009 043 524.7 filed Sep. 30, 2009, the contents of which is incorporated herein by reference in its entirety.

TECHNICAL FIELD

The present invention relates to a device and a process for the photometric examination of samples.

BACKGROUND

Automated analysis instruments, as are routinely used these days in analysis, forensics, microbiology and clinical diagnostics, need to determine different properties of liquids (e.g. in the case of blood clotting examinations) in a quick, precise and reproducible fashion by means of optical processes. In essence, two different measuring principles are currently used in hemostatic analysis instruments. Firstly, use is made of instruments with a stationary detection unit, for example a stationary photometer, and a disk-shaped, moveable sample holder (a so-called sample carousel). The samples in the sample holder are successively led past the detection unit and tested. Accordingly, the sample carousel has to halt every time a new sample is introduced into the carousel or an already tested sample is removed from the carousel. Thus, these steps are accompanied by a significant loss of efficiency. Alternatively, it would be feasible for a gripper to remove samples from the rotating sample carousel; however, such an arrangement is very susceptible to faults.

The other measuring principle utilizes a plurality of stationary optical detection units. Here, respectively one detection unit is provided per sample. This always affords the possibility of measuring a plurality of samples at the same time. However, every detection unit has its own optical setup in this measuring principle, which increases the material and production costs, makes the device susceptible to faults and complicated to service, and moreover harbors the risk of variations in the precision between the individual detection units, which variations are difficult to control.

SUMMARY

According to various embodiments, a device for the photometric examination of samples can be provided, which device avoids the disadvantages of conventional instruments.

According to further embodiments, such a device can be designed such that reagents can be pipetted continuously into the sample vessels during the measurement.

According to an embodiment, a device for the photometric examination of samples may comprise at least a sample-holder apparatus having means for holding at least two sample vessels, a measuring apparatus, and a moveable apparatus, wherein the sample-holder apparatus is designed to be stationary, and the measuring apparatus is arranged on the moveable apparatus and can be displaced by means of the moveable apparatus.

According to a further embodiment, the means for holding the sample vessels can be arranged on the sample-holder apparatus in a linear arrangement and the measuring apparatus can be displaced parallel to the mentioned linear arrangement. According to a further embodiment, the means for holding the sample vessels can be arranged on the sample-holder apparatus in an arc-like arrangement and the measuring apparatus can be displaced rotating around the mentioned arc-like arrangement. According to a further embodiment, the measuring apparatus may have at least one light source and/or at least one photodetector. According to a further embodiment, the light source may have a light emitting diode (LED) or a laser diode (LD). According to a further embodiment, the device may have a plurality of measuring apparatuses. According to a further embodiment, at least one measuring apparatus can be designed such that it can measure continuously during the process with the aid of the moveable apparatus. According to a further embodiment, the moveable apparatus can be arranged below the sample-holder apparatus. According to a further embodiment, the device furthermore may have at least one mixing apparatus arranged on the sample-holder apparatus. According to a further embodiment, the mixing apparatus can be a magnetic mixing apparatus. According to a further embodiment, the device may have a plurality of mixing apparatuses.

According to a further embodiment, a process for the photometric examination of samples, may comprise the use of a device as described above.

According to yet another embodiment, in a process for the photometric examination of samples, at least two sample vessels containing samples can be arranged on a sample-holder apparatus and at least one optical property of the samples can be measured by means of a measuring apparatus, which comprises the sample-holder apparatus being kept stationary and the measuring apparatus being displaced along the arrangement of the sample vessels containing samples by means of a moveable apparatus.

According to a further embodiment of the process, the sample vessels containing samples can be arranged on the sample-holder apparatus in an arc-like fashion and the measuring apparatus can be displaced along the arrangement of the sample vessels containing samples by means of a rotational movement of the moveable apparatus. According to a further embodiment of the process, the rotational frequency of the moveable apparatus may lie in the range between approximately 0.02 and approximately 25 Hz, preferably between approximately 0.2 and approximately 10 Hz. According to a further embodiment of the process, at least one optical property of the samples can be measured continuously. According to a further embodiment of the process, at least one optical property of the samples can be measured by light with a wavelength between approximately 300 nm and approximately 1100 nm. According to a further embodiment of the process, one or more samples can be mixed in the sample vessels before and/or during the photometric examination. According to a further embodiment of the above process, a sample can be mixed by virtue of the fact that a magnetic or ferromagnetic pin is driven in the sample vessel by means of a rotating and/or oscillating electromagnetic field. According to a further embodiment of the process, the mixing speed may lie in a region between approximately 0.01 and approximately 1500 rpm.

According to a further embodiment of one of the above processes, the process may be for the photometric examination of bodily-fluid samples, preferably of blood, plasma and/or serum samples. According to a further embodiment of one of the above processes, the process can be used for hemolysis and/or hemostasis measurements.

According to yet another embodiment, an analysis instrument for the automated examination of liquid samples may comprise at least a device for aliquoting sample liquids in a sample vessel, at least one device for aliquoting reagent liquids in a sample vessel and means for controlling these devices, and a device for the photometric examination of samples as described above.

BRIEF DESCRIPTION OF THE DRAWINGS

The present invention is explained in more detail by means of the figures shown and discussed below. Here, it should be noted that the figures are merely descriptive and not intended to restrict the invention in any way.

FIG. 4 shows a further embodiment of the device for the photometric examination of samples. The embodiment corresponds to that of FIG. 1, with the difference that in this case there are three measuring apparatuses rather than only one.

FIG. 5 shows a further embodiment of the device with a concentric arrangement of the sample vessels in two rows.

FIG. 6 shows a three-dimensional illustration of a device according to various embodiments.

DETAILED DESCRIPTION

Figure 1:
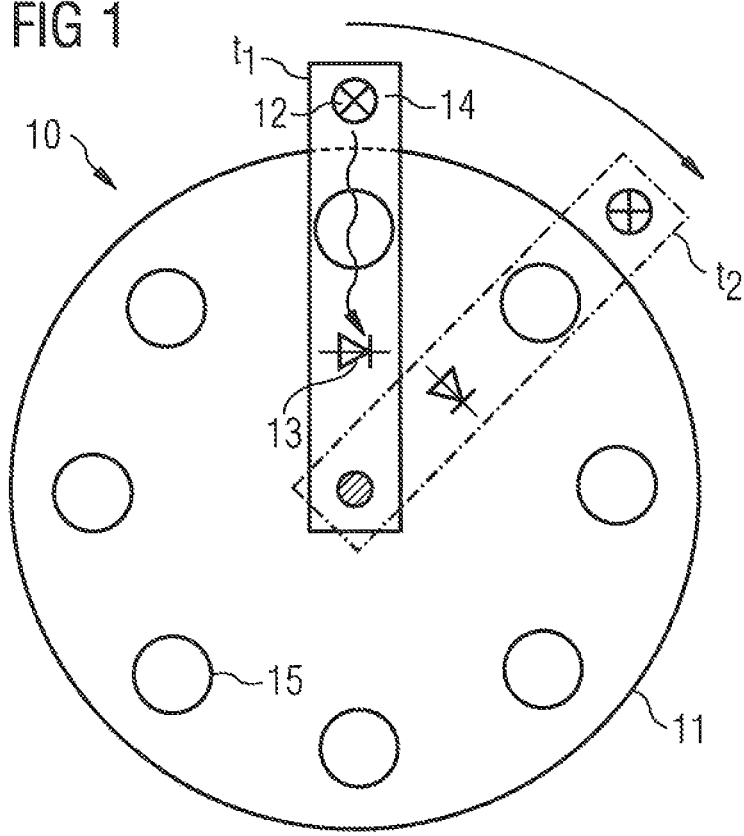
FIG. 1 shows a plan view of an embodiment of the device for the photometric examination of samples. In this embodiment the device only has one measuring apparatus. Additionally, the temporal progression of the measurement is indicated.

According to the various embodiments, provision is made for a device for the photometric examination of samples. Said device has a sample-holder apparatus for at least two sample vessels, and a measuring apparatus and a moveable apparatus. Here, the sample-holder apparatus is designed to be stationary and the measuring apparatus is arranged on the moveable apparatus such that it can be displaced by means of the moveable apparatus.

The term "photometric examination", as used in the present case, relates to absorption, reflection, diffraction, fluorescence, phosphorescence, chemiluminescence and/or scattering measurements using electromagnetic waves. Here, electromagnetic waves from the visible spectrum (with a wavelength between approximately 350 nm and approximately 750 nm) are initially borne in mind, but also waves in the infrared (IR) spectrum (with a wavelength between approximately 750 nm and approximately 1 mm) and in the ultraviolet (UV) spectrum (with a wavelength between approximately 350 nm and approximately 50 nm).

Contrary to conventional devices, there is no longer any need for the sample vessels to be displaced in the device according to various embodiments; rather, it is merely the measuring apparatus or measuring apparatuses that is/are displaced. This firstly may result in the advantage of less mass being moved overall. Additionally, spilling of the liquids or possible movements caused by the displacement, which can both lead to falsification of the measurement results, are avoided in liquid samples.

It is for these reasons that previously known instruments moreover always required the drive speed at which the samples are moved to be adapted and to be correspondingly decelerated, i.e. deceleration and acceleration processes needed to be integrated. Accordingly, a further advantage of the device according to various embodiments is that this necessity can now be dispensed with and hence there can be an increase in the drive speed of the device and, as a result thereof, in the measurement frequency (the number of measurements per second).

Additionally, in contrast to a moveable sample plate, the samples can be heated in a technically simpler fashion in the device according to various embodiments because the electrical supply of the heating element and the sensor system are located on a stationary part.

Moreover, access to each sample is possible at all times in the device according to various embodiments because the sample vessels themselves are not moved. In particular, there is no reliance on sequential testing of the individual sample vessels, but individual sample vessels can be approached and tested in a targeted fashion. More particularly, this allows a change in the displacement direction of the measuring apparatus with little effort; in practice, this can only be implemented with increased complexity using the discussed carousel apparatus from the prior art due to the increased mass.

Furthermore, the device according to various embodiments is advantageous because this arrangement allows virtually continuous and high-frequency measurements. This is explained in more detail below.

In the following text, the term "sample-holder apparatus" should denote an apparatus that can carry and hold at least two sample vessels. For this, the sample-holder apparatus has means for holding at least two sample vessels. By way of example, omissions (bores, stamped holes, depressions) in the body of the sample-holder apparatus, which omissions are formed such that the provided sample vessels can be inserted and removed again in an accurately fitting fashion, are suitable for holding sample vessels. Mechanical means (for example components with a female thread) that allow temporary fixing of appropriately equipped sample vessels (e.g. with a region or component with a male thread) to the sample-holder apparatus are also suitable. More particularly, the sample-holder apparatus can for example allow measuring the samples from below, from the side, from above or a combination of all three options (cf. FIG. 3).

The sample-holder apparatus can be preferably designed such that it can regulate the temperature of the sample in the sample vessel. For this, the sample-holder apparatus preferably may comprise a heat-conducting material and comprises an electrical component that converts electrical energy into heat energy, i.e. a thermal resistor, e.g. in the form of a heating coil, a heating band or a heating sleeve. The sample-holder apparatus particularly preferably may heat the sample to approximately 37° C.

Moreover, a person skilled in the art knows how a sample-holder apparatus has to be designed so that the loading with sample vessels and the removal of sample vessels is conducted in a safe and efficient fashion. The loading of the sample-holder apparatus with sample vessels and the removal of the latter can be brought about manually by a user. Controlled devices such as gripper arms, which can transport the sample vessels, may preferably be provided in an automated analysis instrument.

In the following text, the term "sample vessel" should denote a vessel in which there is the sample to be measured or a sample-reagent mixture. The sample vessel should be designed such that the measurement can be performed in a quick, precise and reproducible fashion. Additionally, the sample vessel should be able to be transported easily within a machine. Cuvettes that consist of a material with low self-absorption, which is transparent to the respectively used wavelength spectrum, and can possibly also be produced cost-effectively may be generally preferred. Said cuvettes can consist of, for example, transparent plastic such as polycarbonate or polymethyl methacrylate. Quartz cuvettes can also be used, particularly for applications in which ultraviolet light is used.

The term "measuring apparatus" denotes an apparatus that comprises an essential component for performing a photometric measurement, i.e. at least one light source or at least one photodetector. A measuring apparatus preferably may comprise at least one light source and at least one photodetector.

In the following text, the term "moveable apparatus" should denote an apparatus that can be moved, i.e. that can drive a measuring apparatus to different positions and thereby allows testing of samples at different positions. In one embodiment, the moveable apparatus is a rod-shaped component that is mounted on an axis and can rotate about this axis (axis of rotation).

Provision can be preferably made for the sample vessels to be arranged on the sample-holder apparatus in a linear arrangement and the measuring apparatus to be able to be displaced parallel to the mentioned linear arrangement with the aid of the moveable apparatus.

Alternatively, provision can be preferably made for the sample vessels to be arranged on the sample-holder apparatus in a concentric arrangement, i.e. in the form of at least two circles arranged concentrically with respect to one another. This allows more sample vessels to be housed on the device (FIG. 5).

Furthermore, provision can be preferably made for the sample vessels to be arranged on the sample-holder apparatus in an arc-like arrangement and the measuring apparatus to be able to be displaced rotating around the arrangement of the sample vessels with the aid of the moveable apparatus.

Here, the sample vessels are arranged like a stationary, non-rotating disk (also referred to as a "cylindrically designed cuvette receptacle" or "cylindrical cuvette receptacle" in the following text) while the measuring apparatus rotates and in the process traces the positions of the individual sample vessels. The axis of rotation of the measuring apparatus preferably may correspond to the center of the arc-like arrangement of the sample vessels or the common center of concentrically arranged sample vessels.

In an embodiment the device has e.g. 25 cuvettes (with an angular spacing of 14.4° between the cuvettes), and the measuring apparatus rotates at 2 Hz, i.e. the contents of each cuvette are measured twice every second. Here, one of the 25 positions can serve as a reference position, in which a reference value or blank is measured.

Furthermore, the measuring apparatus has at least one light source and/or at least one photodetector. The measuring apparatus preferably may have at least one photodetector and at least one light source. In an arc-like arrangement of the cuvettes on a cylindrical cuvette receptacle, the light source or the photodetector could therefore be fixedly arranged around the center of the cylindrical cuvette receptacle, and in each case only one photodetector or one light source would rotate. This could reduce the technical complexity. Additionally, this design also averts the aforementioned risk of accuracy variations between the individual detection units.

It may be furthermore preferable for the light source to have an LED (light-emitting diode). Such a light source has a smaller installation size and a lower weight than other light sources known from the prior art. This leads to significant simplifications in the design and, as a result of the lower weight, reduces possible imbalances that can be caused by a rotation of the measuring apparatus with a large mass. Moreover, LEDs develop little heat, and the wavelength spectrum of LEDs can be defined precisely, and so corresponding cooling and/or filters can possibly be dispensed with, which in turn reduces weight, complexity and installation size, and therefore reduces costs and possibly imbalances. Additionally, there is a large resilience to collisions and shocks and the ability for quick switching and modulating that support the use of an LED.

However, provision can likewise be made for the light source to be a laser diode, with an adapted design, an incandescent lamp, a gas-discharge lamp or an arc lamp.

The photodetector may be preferably a photodiode that converts visible light (in some embodiments also IR or UV light) into an electrical current or voltage by the inner photoelectric effect.

The photodetector alternatively is a CCD sensor. CCD sensors comprise a matrix or a row with light-sensitive photodiodes. The use of a CCD sensor is particularly expedient when the device has more than one measuring apparatus, for example when measurements are intended to be carried out at different wavelengths. Here each element of the CCD sensor can serve as a photodetector for one of the measuring apparatuses, which significantly simplifies the technical design.

However, provision can likewise be made for the photodetector to be a photocell, a silicon photodetector, an avalanche photodetector or a photomultiplier.

In principle, the measuring apparatus can furthermore additionally have filters, optical elements (e.g. lenses for building a condenser), control electronics, evaluation and readout electronics and/or a voltage supply.

The device has a plurality of measuring apparatuses in an embodiment. For this, the plurality of measuring apparatuses may be preferably arranged together on a single moveable apparatus (cf. FIG. 4). Alternatively, provision can be made for a plurality of moveable apparatuses, on which one or more measuring apparatuses are arranged in each case.

As a result, a sample can be measured sequentially at a number of wavelengths. The wavelengths can be preferably in a range from approximately 300 nm to approximately 1100 nm. More particularly, the wavelengths 340 nm, 405 nm, 470 nm, 600 nm and 850 nm may be preferably used in the process because these are particularly suitable for hemostatic examinations.

However, other measurement protocols performed by the device according to various embodiments can also utilize different wavelengths. A person skilled in the art knows which wavelengths should be used for a particular measurement.

Hemostasis is understood to be the vitally important process that stops the bleeding occurring when the blood vessels are injured. The hemostasis system is characterized by two opposing objects. On the one hand, a continuous flow of the blood must be ensured by constant anticoagulation, and, on the other hand, when required, the hemostasis (i.e. the blood clotting) must be induced as quickly as possible and must be limited precisely to the location of the injury.

Special tests are used for determining the ability to clot, in which tests the activity of a single or a number of blood clotting factors is determined by measuring the speed of fibrination in a blood or plasma sample. Typical examples of such clotting tests are the prothrombin time (PT) (also referred to as Quick's test or thromboplastin time), the activated partial thromboplastin time (APTT), the thrombin time (TT), the batroxobin time (BT) or the ecarin clotting time (ECT).

Since the actual detection reaction is bound to the polymerization of the initially soluble fibrin to insoluble high-polymer fibrin, the selection of the wavelength at which the photometric measurement takes place is important. In general, wavelengths in excess of 500 nm are selected for the measurement. This minimizes the most-common disturbances in the sample (bilirubin and hemoglobin).

Hemolysis is understood to be the breaking up of erythrocytes by destroying the cell membrane, and the release of hemoglobin and other cytoplasmatic components (e.g. lactate dehydrogenase) connected therewith.

In the case of hemolytic blood, the separation of plasma and erythrocytes allows photometric quantification of e.g. the content of hemoglobin in the plasma. The photometric determination of blood is a standard method in medicine. Thus, hemolysis can be used as an indicator for different underlying diseases including immune response against membrane components, toxic destruction, parasites, bacterial enzymes and structural peculiarities.

The variables to be determined in hemolysis or hemostasis measurements comprise e.g. haptoglobin, reticulocytes, indirect bilirubin, LDH and potassium (in the case of massive hemolysis).

In the case of the cyanmethemoglobin method, all forms of hemoglobin (Hb) are converted into stable cyanmethemoglobin (HbCN) after eliminating scattering cell components, which is connected with a change in the spectral absorption coefficient independent of the previous reduced or oxygenated state. The characteristic absorption spectra of oxygenated and reduced hemoglobin at the isosbestic wavelength allow the quantitative determination of the oxygen saturation in the blood. Furthermore, it is also possible for the concentrations of the hemoglobin derivatives HbCO (carboxyhemoglobin), MetHb (methemoglobin) and HbF (fetal hemoglobin) to be determined on the basis of their specific absorption spectra. By way of example, an increased value of HbCO can be determined in the case of carbon monoxide poisoning, and an increased value of MetHb can be determined in the case of nitrite or nitrogen oxide inhalation.

Depending on the examined variable, different wavelengths are used in hemolysis or hemostasis measurements. By way of example, the indicator reaction of lactate dehydrogenase (reduction of NADH) preferably may take place at 340 nm.

In the case of an arc-like arrangement of the sample vessels, the plurality of measuring apparatuses can be arranged in a uniform, circumferentially arranged array on a moveable apparatus (see FIG. 4).

Such an arrangement results in particularly smooth running properties of the displaceable measuring apparatus(es), and simplifications can be implemented in the measured value analysis.

Furthermore, it may be preferable for at least one measuring apparatus to be designed such that it can measure continuously or virtually continuously during the process with the aid of the moveable apparatus.

In such an embodiment, evaluation electronics or the subsequent control software always knows and determines the spatial arrangement of measuring apparatus and the at least two sample vessels with respect to one another, e.g. by means of known angles or by means of trigger signals, by means of which e.g. a stepper motor displacing the measuring apparatus is controlled. Therefore, the electronics can at all times assign the generated signal, e.g. an absorption signal, to a certain location (i.e. e.g. a certain cuvette). By way of example, a distinction can thus be made between signals generated by glass edges or air interspaces and actual measurement signals generated by a sample (see FIG. 2).

The term "measure continuously", as used in this context, refers to an analog readout of the measuring apparatus. However, this can also likewise mean a virtually continuous digital readout with a high readout rate, for example >1000 Hz.

Provision can moreover be made for at least part of the obtained measured values to be averaged over a certain time window in order to increase the measurement accuracy.

In an embodiment, the moveable apparatus is arranged below the sample-holder apparatus (see FIG. 3). This affords the simplest combination of access to all cuvettes, advantageously possible at all times, and the continuous measurement. This additionally allows more or less continuous pipetting of reagents into the sample vessels during the measurement procedure.

The moveable apparatus is arranged above the sample-holder apparatus in other embodiments. In such a refinement, the sample vessels could for example be introduced into the sample-holder apparatus from below. This would allow access to the sample vessels at all times, but this embodiment does not allow continuous adding of liquids to the sample vessels.

Moreover, provision can be preferably made for the device to have at least one mixing apparatus arranged on the sample-holder apparatus.

Although hemolysis and hemostasis measurements in particular do not always require continuous mixing of the sample during the measurement (this is even undesirable in some cases), there are test requirements in which mixing is expedient, e.g. in the case of particularly turbid samples or in the case of platelet aggregometry.

The mixing apparatus may be preferably a magnetic mixing apparatus. In this embodiment, the mixing apparatus can comprise e.g. a rotating drive magnet or other means that generate a rotating and/or oscillating electromagnetic field. A magnetic mixing apparatus acts on a second magnetic or ferromagnetic body, e.g. in the form of a rod-shaped stirrer or in the form of particles (so-called beads) contained in a sample vessel, and it sets the latter into motion, as a result of which the sample liquid or the sample-reagent mixture is mixed in the sample vessel.

However, other mixing apparatuses are also feasible, for example an apparatus that mixes using ultrasound and hence does not require magnetic or ferromagnetic bodies in the sample vessel. A mixing apparatus can likewise have a rotating eccentric or a loudspeaker by means of which oscillations can be transmitted to the sample vessels.

The device preferably may have a plurality of mixing apparatuses. In the case of the aforementioned arc-like arrangement of the sample vessels with one or more measuring apparatuses, mixing apparatuses can be arranged at e.g. 4 of 25 positions for sample vessels. Such an embodiment has proven its worth particularly for hemolysis or hemostasis measurements because mixing is not required for all test requirements.

A further subject matter of the various embodiments is an analysis instrument for the automated examination of liquid samples, which analysis instrument comprises a device according to various embodiments for the photometric examination of samples. Such analysis instruments for the automated examination of liquid samples usually comprise at least one device for aliquoting sample liquids in a sample vessel, e.g. in the form of a first automatic pipettor, at least one device for aliquoting reagent liquids in a sample vessel, e.g. in the form of a second automatic pipettor, and means for controlling these devices (software, computer program, algorithm).

Moreover, a process for the photometric examination of samples, which uses a device according to various embodiments for the photometric examination of samples, may be preferred.

Such a process, in which the device is part of an analysis instrument, could for example proceed as follows: the sample-holder apparatus is firstly loaded with sample vessels, e.g. cuvettes, which are subsequently filled at a pipetting station with liquid samples, e.g. blood, plasma and/or serum. In the next step, an analysis reagent is added at a pipetting station. Since a mixing of the samples prior to measuring is necessary in this example, the sample is, in accordance with the settings of the analysis instrument, mixed by a mixing apparatus, in this case a rotating magnet, before it is tested by a measuring apparatus, in this case a photometer. In this example, the cuvettes are arranged in an arc-like fashion and five photometers drive around the cuvettes at a rate of 2 Hz. During the measurement, the sample is irradiated by light from an LED in the photometer. The photodetector of the photometer in this case is a photodiode. An electrical signal is generated therein that is proportional to the intensity of the light passing through the cuvette. After a sample was tested, the cuvette in which the sample is located is transported further to another instrument, for example to a cooling apparatus or to a PCR instrument, or the cuvette is disposed of in a waste vessel. The position of the removed cuvette is replaced by a cuvette containing a new sample.

As an alternative to the procedure just described in an exemplary fashion, the samples can already be located in the sample vessels when the sample-holder apparatus is being loaded with the latter and/or the measuring process is commenced immediately without there being mixing in advance.

Thus, a further subject matter of the various embodiments is a process for the photometric examination of samples, wherein at least two sample vessels containing samples are arranged on a sample-holder apparatus and wherein at least one optical property of the samples is measured by means of a measuring apparatus and wherein the sample-holder apparatus is kept stationary and the measuring apparatus is displaced along the arrangement of the sample vessels containing samples by means of a moveable apparatus.

In an embodiment, the sample vessels containing samples are arranged on the sample-holder apparatus in an arc-like fashion and the measuring apparatus is displaced along the arrangement of the sample vessels containing samples by means of a rotational movement of the moveable apparatus. The rotational frequency of the moveable apparatus preferably may lie in the range between approximately 0.02 and approximately 25 Hz, particularly preferably between approximately 0.2 and approximately 10 Hz.

In a further embodiment of the process, at least one optical property of the samples is measured continuously. This can be performed by reading out the measuring apparatus in an analog fashion, but also by a readout in a virtually continuous digital fashion with a high readout rate, for example >1000 Hz.

In a further embodiment of the process, at least one optical property of the samples is measured by light with a wavelength between approximately 300 nm and approximately 1100 nm. The wavelength preferably may lie at 340 nm, 405 nm, 470 nm, 600 nm, 800 nm or 850 nm.

In a further embodiment of the process, one or more samples or sample-reagent mixtures are mixed in the sample vessels before and/or during the photometric examination. The sample can be mixed by virtue of the fact that a magnetic or ferromagnetic pin is driven in the sample vessel by means of a rotating and/or oscillating electromagnetic field. The mixing speed preferably may lie in a region between approximately 0.01 and approximately 1500 rpm (rotations per minute).

The process according to various embodiments may be particularly suitable for the photometric examination of bodily-fluid samples, preferably of blood, plasma and/or serum samples and can preferably be used to determine clotting and/or fibrinolysis parameters, i.e. for hemolysis and/or hemostasis measurements.

FIG. 1 shows a schematic illustration of the device according to various embodiments for the photometric examination of samples. In this example, the device 10 is part of an analysis instrument. It has a sample-holder apparatus in the form of a cylindrical cuvette receptacle 11 with eight means 15 for holding sample vessels, a measuring apparatus (in this case a photometer), which has an LED 12 and a photodiode 13, and a moveable apparatus 14. The cylindrical cuvette receptacle 11 is designed to be stationary and the LED 12 and the photodiode 13 are arranged on the moveable apparatus 14 such that the LED 12 drives around the cuvettes positioned in the holding means 15 on the outside and the photodiode 13 drives around the cuvettes on the inside. The measuring unit made of LED 12 and photodiode 13 continuously measures the intensity of the light beam passing through the sample for the photometric examination of samples in the cuvettes, and it thereby measures the absorption (if a corresponding reference variable is known). In the process, the moveable unit moves, for example, continuously in a clockwise direction at a rate of 2 Hz. Thus a sample is measured at time $t_1$, and the next sample is measured at time $t_2$.

The moveable apparatus can alternatively also move counterclockwise or change the direction of movement. Likewise, the measuring apparatus can alternatively also carry out reflection, diffraction, fluorescence, phosphorescence and/or scattering measurements. A person skilled in the art knows how the measuring apparatus has to be designed in the specific case for these other measuring principles.

Figure 2:
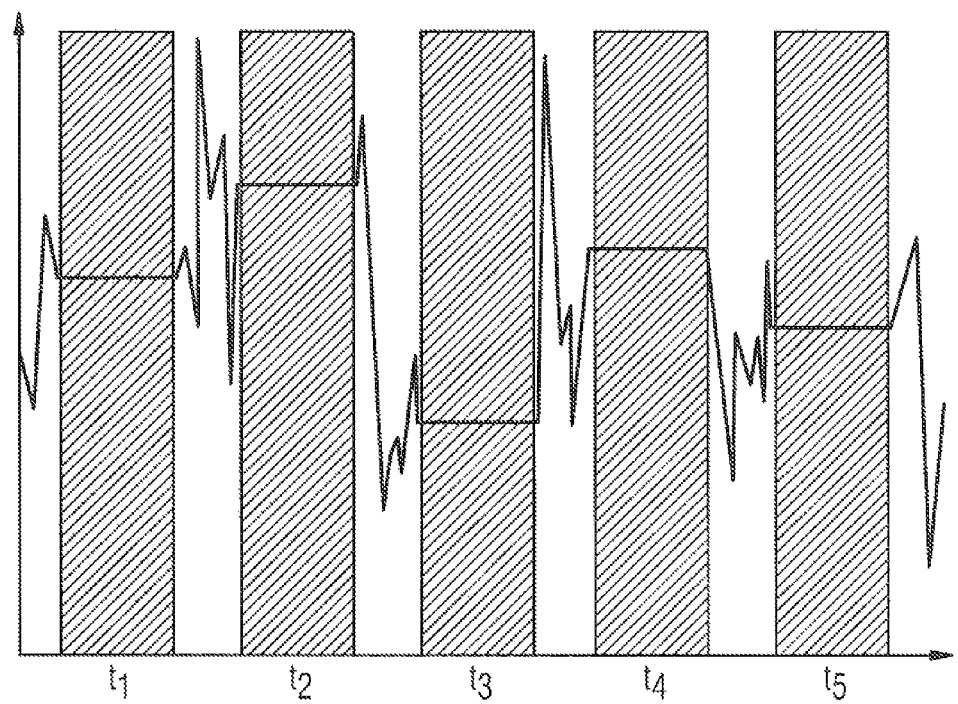
FIG. 2 shows a schematic illustration of the temporal progression of the measuring procedure as per FIG. 1.

FIG. 2 shows a schematic illustration of the continuous measuring procedure as per FIG. 1. The gray bars in each case represent the period of time during which the measurement beam of the measuring apparatus passes a cuvette. At the time $t_1$, during which the contents of a cuvette, i.e. a sample, are just being tested, the measured signal is constant. By contrast, if the measurement beam is currently located between two cuvettes, the generated signal is significantly more heterogeneous because the light from the LED is refracted at glass edges of the cuvettes or in air interspaces. As soon as a cuvette position is reached again, in this case $t_2$ (cf. FIG. 1), the signal becomes more homogeneous again.

The evaluation software can thereby assign the measured values to the cuvettes (samples) and distinguish between measured values belonging to samples and those recorded between samples.

Alternatively, evaluation electronics always know the spatial arrangement of measuring apparatus and sample vessels to one another, e.g. using known angles and angular speeds, and can therefore always assign the generated signal to a specific location. By way of example, this allows a distinction to be made between signals generated by glass edges or air interspaces and actual measurement signals generated by a sample.

Provision can moreover be made for at least part of the obtained measured values to be averaged over a certain time window in order to increase the measurement accuracy.

In the case of a sample-holder apparatus with 25 cuvettes and a rotational frequency of 2 Hz, the measurement beam for example passes each cuvette twice a second.

If the measurement signal is recorded with a sampling rate of 1 kHz, 500 measured values are thus recorded per rotation, part of which (for example 50%) was generated between the cuvettes or on the glass edges thereof. It follows that 250 evaluable, i.e. "real", measured values are recorded per rotation, which corresponds to 10 "real" measured values per cuvette in the case of 25 cuvettes in the sample-holder apparatus 10. Provision can in this case for example be made for the respectively first three "real" measured values to be discarded, the next four to be averaged and the last three to be discarded again. Here the measurement signal is recorded at such a high sampling rate that the photometer can record a sufficient number of measured values required for determining the measured variable when said photometer moves past the position of the stationary cuvette.

If the process according to various embodiments is intended to be carried out with a plurality of measuring apparatuses (for example at different wavelengths), the above-described process is simultaneously carried out on two sampling channels.

Current technology moreover allows significantly higher sampling rates, which ultimately allows higher measurement accuracy due to broader averaging.

Figure 3:
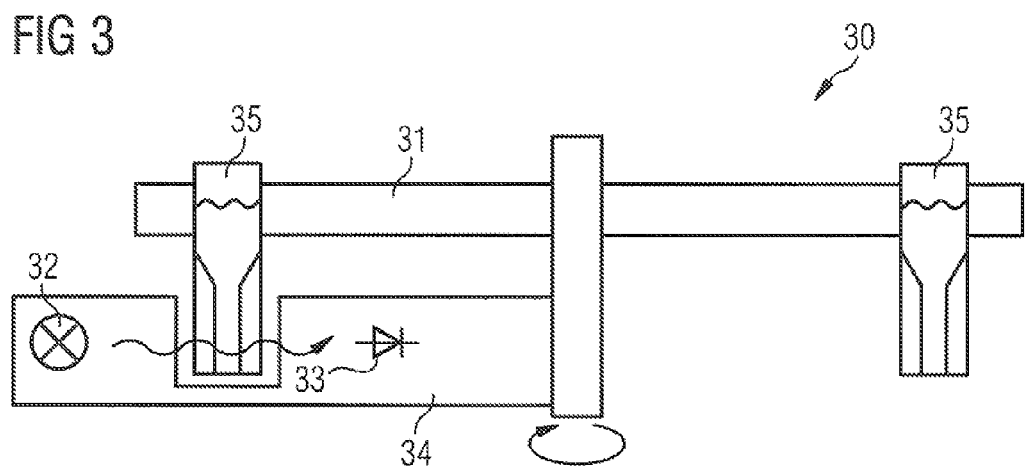
FIG. 3 shows a cross section of the device as per FIG. 1.

FIG. 3 shows a cross section of a device according to various embodiments for the photometric examination of samples. In this example the device 30 has a sample-holder apparatus in the form of a cylindrical cuvette receptacle 31 for cuvettes 35, a measuring apparatus in the form of a photometer, which has an LED 32 and a photodiode 33, and a moveable apparatus 34. The cylindrical cuvette receptacle 31 is designed to be stationary and the LED 32 and the photodiode 33 are arranged on the moveable apparatus 34, wherein the LED drives around the cuvettes 35 on the outside and the photodiode 33 drives around the cuvettes 35 on the inside during the measurement. The moveable apparatus 34 is arranged below the cylindrical cuvette receptacle 31. This allows e.g. a gripper arm to grip the cuvettes 35 at all times.

FIG. 4 shows a further embodiment of the device for the photometric examination of samples. The embodiment corresponds to that of FIG. 1, with the difference that there are three measuring apparatuses in this case rather than just one. In more detail, the device 40 has a sample-holder apparatus in the form of a cylindrical cuvette receptacle 41 with eight means 45 for holding sample vessels in the form of cuvettes, three measuring apparatuses in the form of photometers, which each have one LED 42 and one photodiode 43, and one moveable apparatus 44. The LEDs expediently emit different wavelengths so that the samples can be measured at a number of wavelengths. The cylindrical cuvette receptacle 41 is designed to be stationary and the LEDs 42 and the photodiodes 43 are arranged on the moveable apparatus 44 such that the LEDs 42 drive around the cuvettes positioned in the holding means 45 on the outside and the photodiodes 43 drives around the cuvettes on the inside. Alternatively, the moveable apparatus can have more than three measuring apparatuses (for example five). The photodiodes can alternatively be replaced by a CCD element.

FIG. 5 shows a further embodiment of a device with a concentric arrangement of the sample vessels in two rows. Here, the device 50 has a sample-holder apparatus in the form of a cylindrical cuvette receptacle 51 with sixteen means 55 for holding sample vessels in the form of cuvettes, a measuring apparatus, which has an LED 52 and a photodiode 53, and one moveable apparatus 54. The cylindrical cuvette receptacle 51 is designed to be stationary. By arranging the cuvettes in two concentric annuli the cuvette density and thus the number of samples to be examined can be increased overall.

FIG. 6 shows a three-dimensional illustration of a device 60 according to various embodiments. It has a sample-holder apparatus in the form of a cylindrical cuvette receptacle 61 for twenty-five sample vessels in the form of cuvettes 65, and five measuring apparatuses, each comprising an outer holder 62 for holding a photodetector in the form of a photodiode and an inner holder 72 for holding a light source in the form of an LED, which are arranged on a common moveable apparatus. The cylindrical cuvette receptacle 61 has a stationary design. The moveable apparatus is arranged below the cylindrical cuvette receptacle 61. This is the easiest way of combining the advantageous possible access to all cuvettes at all times with the continuous measuring. What is more, this allows more or less continuous pipetting of reagents into the sample vessels during the measuring procedure.

Deviating from the figures, provision can also be made for the LEDs to drive around the cuvettes on the inside and the photodiodes to drive around the cuvettes on the outside.

It is understood that the alternative embodiments shown in FIGS. 1, 4, 5 and 6 can be individually or multiply combined with one another.

EXAMPLES

The device according to an embodiment was implemented as follows in order to demonstrate the feasibility and operability.

In this example, an $(I, I_0)$ absorption or extinction/turbidity measurement is performed in order to monitor hemostasis in a blood sample. The sample-holder apparatus is designed for 25 cuvettes, which are arranged in an arc-like fashion on the sample-holder apparatus. Respectively one mixing apparatus in the form of a magnetic stirrer is arranged at 4 positions of the sample-holder apparatus. Additionally, the device contains five photometers, respectively one for the measurement at the wavelengths of 340 nm, 405 nm, 470 nm, 600 nm and 850 nm.

| Wavelength | Measured variable |
|---|---|
| 340 nm | NADH |
| 405 nm | p-nitroaniline for detecting thrombin |
| 470 nm | Hemoglobin |
| 600 nm | Coagulation test |
| 850 nm | Turbidity measurement |

The photometers are arranged on a moveable apparatus that drives around the sample vessels at a rate of 2 Hz. The drive may be preferably brought about by means of a stepper motor.

One of the 25 sample vessels serves as control vessel for determining $I_0$ and is therefore filled with merely a reference solution. The readout rate of the measuring apparatuses is 150 kHz, i.e. 3000 measured values are recorded per cuvette and revolution at a predetermined orbit. A central window is defined therefrom, from which an average value is calculated in turn, which average value reflects the absorption of the sample for the given wavelength.

| LIST OF REFERENCE SIGNS | |
|---|---|
| 10 | Device for the photometric examination of samples |
| 11 | Sample-holder device in the form of a cylindrical cuvette |

-continued

LIST OF REFERENCE SIGNS

| | |
|---|---|
| | receptacle |
| 12 | Light source in the form of an LED |
| 13 | Photodetector in the form of a photodiode |
| 14 | Moveable apparatus |
| 15 | Means for holding sample vessels |
| 30 | Device for the photometric examination of samples |
| 31 | Sample-holder device in the form of a cylindrical cuvette receptacle |
| 32 | Light source in the form of an LED |
| 33 | Photodetector in the form of a photodiode |
| 34 | Moveable apparatus |
| 35 | Sample vessel in the form of a cuvette |
| 40 | Device for the photometric examination of samples |
| 41 | Sample-holder device in the form of a cylindrical cuvette receptacle |
| 42 | Light source in the form of an LED |
| 43 | Photodetector in the form of a photodiode |
| 44 | Moveable apparatus |
| 45 | Means for holding sample vessels |
| 50 | Device for the photometric examination of samples |
| 51 | Sample-holder device in the form of a cylindrical cuvette receptacle |
| 52 | Light source in the form of an LED |
| 53 | Photodetector in the form of a photodiode |
| 54 | Moveable apparatus |
| 55 | Means for holding sample vessels |
| 60 | Device for the photometric examination of samples |
| 61 | Sample-holder device in the form of a cylindrical cuvette receptacle |
| 62 | Outer holder for holding a photodetector |
| 65 | Sample vessel in the form of a cuvette |
| 72 | Inner holder for holding a light source |

What is claimed is:

1. A device for the photometric examination of samples, comprising:
    an apparatus configured to hold at least two sample vessels in a linear arrangement or an arc-like arrangement,
    a measuring apparatus comprising at least one light source and at least one photodetector, and
    a moveable apparatus,
    wherein the apparatus configured to hold the at least two sample vessels is configured to be stationary, and
    wherein the measuring apparatus is arranged on the moveable apparatus and configured to displace the measuring apparatus parallel to the linear arrangement or to rotate the measuring apparatus around the arc-like arrangement.

2. The device according to claim 1, wherein the measuring apparatus has exactly one light source and exactly one photodetector.

3. The device according to 2, wherein the light source comprises at least one light-emitting diode (LED) or laser diode (LD).

4. The device according to claim 1, wherein the device has a plurality of measuring apparatuses.

5. The device according to claim 1, wherein the measuring apparatus is configured to measure continuously during movement of the moveable apparatus.

6. The device according to claim 1, wherein the moveable apparatus is arranged below the sample-holder apparatus.

7. The device according to claim 1, wherein the device furthermore has at least one mixing apparatus arranged on the sample-holder apparatus.

8. The device according to claim 7, wherein the mixing apparatus is a magnetic mixing apparatus.

9. The device according to claim 7, wherein the device has a plurality of mixing apparatuses.

10. An analysis instrument for the automated examination of liquid samples, comprising:
    at least a device for aliquoting sample liquids in a sample vessel,
    at least one device for aliquoting reagent liquids in a sample vessel and means for controlling these devices, and
    a device comprising:
        an apparatus configured to hold at least two sample vessels in a linear arrangement or an arc-like arrangement,
        a measuring apparatus having at least one light source and at least one photodetector, and
        a moveable apparatus,
        wherein the apparatus configured to hold the at least two sample vessels is configured to be stationary, and
        wherein the measuring apparatus is arranged on the moveable apparatus and configured to displace the measuring apparatus parallel to the linear arrangement or to rotate the measuring apparatus around the arc-like arrangement.

11. The analysis instrument according to claim 10, wherein the measuring apparatus has exactly one light source and exactly one photodetector.

12. The analysis instrument according to claim 10, wherein the measuring apparatus is configured to measure continuously during movement of the moveable apparatus.

13. The analysis instrument according to claim 12, wherein the light source comprises at least one light-emitting diode (LED) or laser diode (LD).

14. The analysis instrument according to claim 10, wherein the moveable apparatus is arranged below the sample-holder apparatus.

15. The analysis instrument according to claim 10, wherein the measuring apparatus includes at least one of multiple light sources and multiple photo detectors.

16. The device according to claim 1, wherein the measuring apparatus includes at least one of multiple light sources and multiple photodetectors.

* * * * *